United States Patent [19]

Suresh et al.

[11] 4,052,418

[45] Oct. 4, 1977

[54] PREPARATION OF MALEIC ANHYDRIDE FROM FOUR-CARBON HYDROCARBONS

[75] Inventors: Dev D. Suresh, Macedonia; Noel J. Bremer, Stow; Robert K. Grasselli, Chagrin Falls, all of Ohio

[73] Assignee: The Standard Oil Company, Cleveland, Ohio

[21] Appl. No.: 602,343

[22] Filed: Aug. 6, 1975

[51] Int. Cl.² .................... C07D 307/60; B01J 21/02; B01J 23/16; B01J 23/84

[52] U.S. Cl. ............... 260/346.74; 252/432; 252/467; 252/468

[58] Field of Search ............. 260/346.8 A; 252/432, 252/467, 468

[56] References Cited

U.S. PATENT DOCUMENTS

| | | | |
|---|---|---|---|
| 3,156,705 | 11/1964 | Kerr | 260/346.8 A |
| 3,366,648 | 1/1968 | Kerr | 260/346.8 A |
| 3,544,616 | 12/1970 | Grasselli et al. | 252/432 X |
| 3,579,574 | 5/1971 | Van der Meer | 252/467 X |
| 3,856,824 | 12/1974 | Raffelson et al. | 260/346.8 A |
| 3,862,146 | 1/1975 | Boghosian | 260/346.8 A |
| 3,867,411 | 2/1975 | Raffelson et al. | 260/346.8 A |
| 3,888,886 | 6/1975 | Young et al. | 260/346.8 A |
| 3,907,834 | 9/1975 | Milberger et al. | 260/346.8 A |

*Primary Examiner*—Patrick P. Garvin
*Assistant Examiner*—William G. Wright
*Attorney, Agent, or Firm*—Larry W. Evans; Herbert D. Knudsen; Gwenetta D. Hill

[57] ABSTRACT

Catalysts comprising the combined oxides of vanadium and at least one element selected from the group consisting of boron, niobium, tantalum, antimony, tungsten and chromium have been found to be especially effective in the oxidation of n-butane, n-butenes and butadiene, or a mixture thereof with molecular oxygen in the vapor phase to yield maleic anhydride. The catalysts of the present invention may be further promoted with additional elements to enhance activity, stability and selectivity. The reaction with n-butane gives an especially pure product in good yield and selectivity.

9 Claims, No Drawings

PREPARATION OF MALEIC ANHYDRIDE FROM FOUR-CARBON HYDROCARBONS

SUMMARY OF THE INVENTION

It has been discovered in the process for the production of maleic anhydride by the oxidation of n-butane, n-butenes, butadiene or a mixture thereof with molecular oxygen in the vapor phase at an elevated temperature of about 300° C to about 600° C in the presence of a catalyst comprising the combined oxides of vanadium and at least one element selected from the group consisting of boron, niobium, tantalum, antimony, tungsten and chromium.

The most significant aspect of the present invention is the catalyst. The catalyst, as noted, may be optionally promoted with additional elements to enhance its activity, stability and selectivity. Preferred catalysts are described by the following formula:

$$A_a V_b D_c O_x$$

wherein A is at least one element selected from the group consisting of an alkali metal, zinc, cadmium, phosphorus, arsenic, copper, cerium, thorium, tin, manganese, iron and uranium;

D is at least one element selected from the group consisting of boron, niobium, tantalum, antimony, tungsten and chromium;

and wherein a is 0 to 5;

b and c are 0.1 to 10; and x is the number as determined by the combined valence requirement of elements other than oxygen present in the catalyst.

The present invention is an improved process for the production of maleic anhydride from four-carbon paraffins by the use of a new catalyst. Maleic anhydride is produced in a simple manner at a low cost by the oxidation of inexpensive paraffins. The stability and activity of the catalyst is improved; and unlike most processes that deal with the catalytic vapor oxidation of paraffins to produce maleic anhydride, the catalyst composition does not require phosphorus as an essential element. The process of the present invention is especially effective in the production of maleic anhydride from n-butane in good yields. Also, the catalysts of the present invention are useful in the production of phthalic anhydride from xylenes.

The catalysts may be prepared by a number of known methods. The catalysts are conveniently prepared by digesting oxides or salts of the various ingredients of the cataysts in concentrated hydrochloric acid. Other methods such as combining the oxides or nitrates are also acceptable. The most preferred preparation is described in the Specific Embodiments.

The catalysts may be used alone or a support could be employed. Suitable supports include silica, alumina, Alundum, silicon carbide, boron phosphate, zirconia and the like. The catalysts are conveniently used in a fixed-bed reactor using tablets, pellets or the like or in a fluid-bed reactor using a catalyst preferably having a particle size of less than about 300 microns.

The process for preparing maleic anhydride by reacting the hydrocarbon with molecular oxygen in the vapor phase in the presence of a catalyst is known. The hydrocarbon reacted by the process of the present invention may be n-butane, n-butenes, butadiene or mixture thereof. Preferred is the use of n-butane or a mixture of hydrocarbons that are produced in refinery streams. The molecular oxygen is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. The ratio of the hydrocarbon to molecular oxygen may range from about 2 to about 30 moles of oxygen per mole of hydrocarbon. The higher oxygen ratios are associated with fixed-bed reactors and are used to avoid the explosive range of the reactants. Preferred oxygen ratios are about 4 to about 20 moles per mole of hydrocarbon.

The reaction temperature may vary widely and is dependent upon the particular hydrocarbon and catalyst employed. Suitably, a temperature within the range of about 300° C to about 600° C gives the best results. The reaction can be conducted at atmospheric, superatmospheric or subatmospheric pressure.

SPECIFIC EMBODIMENTS

EXAMPLE 1 TO 17

Preparation of maleic anhydride using various catalysts of the invention.

Catalysts of the invention were prepared as follows:

EXAMPLE 1

$$Zn_{0.2}V_1B_{1.2}O_x$$

45.5 g. of vanadium pentoxide was digested in 295 cc. of concentrated HCl and the mixture was heated on a hot plate with constant stirring for about one-half hour, an aqueous solution containing 13.6 g. of zinc chloride was added. Heating and stirring was continued about 15 minutes. An aqueous slurry containing 37.1 g. of boric acid was added to the mixture and heated with constant stirring until the mixture solidified. The catalyst was dried at about 120° C.

EXAMPLE 2

$$Zn_{0.2}V_1B_1Sb_{0.2}O_x$$

22.4 g. of vanadium pentoxide was digested in 295 cc. of concentrated HCl and refluxed for 4 hours, 7.29 g. of antimony trioxide was added to this solution, followed by the addition of an aqueous solution containing 15.5 g. of boric acid, and an aqueous solution containing 6.8 g. of zinc chloride. The mixture was refluxed for 2 hours and was slowly evaporated to dryness.

EXAMPLE 3

$$V_1Nb_1Sb_{0.2}O_x$$

A vandium-containing solution was prepared in the same manner as Example 2.

33.3 of niobium pentoxide was mixed with 6.1 g. of antimony metal powder in $H_2O$. HCl was slowly added of this solution with constant stirring and the bulk was added to the vanadium-containing solution. The mixture was refluxed for 6 hours. The color changed to pale-green. The catalyst was evaporated to dryness.

EXAMPLE 4

$V_{1.0}W_{1.2}Zn_{0.2}O_x$

A vanadium-containing solution was prepared in the same manner as Example 2.

75.0 g. of tungstic acid was added to 3.27 g. of zinc metal powder in water, the bulk color changed to blue; dilute HCl was added. This mixture was added to the vanadium-containing solution. The color changed from blue to yellowish-green. The bulk was slowly evaporated to dryness.

EXAMPLE 5

$Zn_{0.2}V_{1.0}Sb_{1.2}As_{0.1}O_x$

This catalyst was prepared in the same manner as Example 2 using these compounds in amounts as follows:

298 cc HCl (conc.)

22.7 g. of $V_2O_5$
6.8 g. of $ZnCl_2$
43.7 g. of $Sb_2O_3$
3.8 g. of $H_3AsO_4 \cdot \frac{1}{2}H_2O$

EXAMPLE 6

$Zn_{0.2}V_1Nb_{1.2}O_x$

This catalyst was prepared in the same manner as Example 5 except the antimony trioxide and arsenic acid were replaced by 39.9 g. of niobium pentoxide.

EXAMPLE 7

$K_{0.02}[Zn_{0.2}V_1Nb_{1.2}O_x]$

This catalyst was prepared by impregnating the catalyst of Example 6 as follows: 5.5 g. of the catalyst were heated with $2.4 \times 10^{-4}$ g. of potassium hydroxide in 1.5 mls. of distilled $H_2O$.

EXAMPLES 8 to 17

The catalysts were prepared in the same manner as shown above using the appropriate ratio of ingredients.

The catalysts prepared above were ground and screened to recover these particles of 20 to 32 mesh size. A portion of these catalyst particles were placed in a 5 cc. fixed bed reactor constructed of a length of 12.7 cm. stainless steel tubing having a 1.0 cm. inside diameter and heated under a flow of air for 16 hours at 290°

The reactor was heated to the reaction temperature and a feed of 1 n-butane/50 air was fed over the catalyst at an apparent contact time of 1.0 second. The reactor was run under the reaction conditions for 2 hours to pre-condition the catalyst. The reactor effluent was collected and analysed by gas chromatography.

The results are stated in terms of single pass yield which is defined as $$\frac{\text{Moles of Maleic anhydride obtained}}{\text{Moles of n-butane in the feed}} \times 100$$

and the total conversion defined as $$\frac{\text{Moles of n-butane reacted}}{\text{Moles of n-butane in the feed}} \times 100$$

and the selectivity defined as $$\frac{\text{Single Pass Yield}}{\text{Total Conversion}} \times 100$$

The experimental results are shown in the Table below.

TABLE

Preparation of Maleic Anhydride from n-Butane

| EXAMPLE | CATALYST | REACTION TEMP. ° C | N-BUTANE CONVERSION | SINGLE PASS YIELD | SELECTIVITY |
|---|---|---|---|---|---|
| 8 | $Zn_{0.2}V_{1.0}B_{1.2}O_x$ | 450 | 18.2 | 10 | 55 |
| 9 | $Zn_{0.2}V_{1.0}B_{1.2}O_x$ | 500 | 21.2 | 14 | 66 |
| 10 | $Zn_{0.2}V_1B_1Sb_{0.2}O_x$ | 480 | No data | 1.2 | No data |
| 11 | $Zn_{0.2}V_1B_1Sb_{0.2}O_x$ | 540 | 6.1 | 4.6 | 86.0 |
| 12 | $V_1Nb_1Sb_{0.2}O_x$ | 450 | No data | 3.8 | No data |
| 13 | $V_{1.0}W_{1.2}Zn_{0.2}O_x$ | 450 | No data | 1.6 | No data |
| 14 | $Zn_{0.2}V_{1.0}Sb_{1.2}As_{0.1}O_x$ | 400 | 98.7 | 7.2 | 7.3 |
| 15 | $Zn_{0.2}V_{1.0}Nb_{1.2}O_x$ | 450 | 58.6 | 22.5 | 38.5 |
| 16 | $Zn_{0.2}V_{1.0}Nb_{1.2}O_x$ | 500 | 93.6 | 32 | 34.2 |
| 17 | $K_{0.02}[Zn_{0.2}V_{1.0}Nb_{1.2}O_x]$ | 500 | 80.8 | 12.6 | 15.6 |

We claim:

1. In the process for the preparation of maleic anhydride by the oxidation of n-butane, n-butenes, butadiene or mixture thereof with molecular oxygen in the vapor phase at a reaction temperature of about 300° C to about 600° C in the presence of a catalyst, the improvement comprising using as a catalyst a catalyst of the formula:

$$A_aV_bD_cO_x$$

wherein
A is at least one element selected from the group consisting of an alkali metal, zinc, cadmium, arsenic, copper, cerium, thorium, tin, manganese, iron and uranium; and D is at least one element selected from the group consisting of boron, niobium, tantalum, antimony, tungsten and chromium;
and wherein
$a$ is 0 to 5;
$b$ and $c$ are 0.1 to 10; and
$x$ is the number as determined by the combined valence requirements of elements other than oxygen present in the catalyst.

2. The process of claim 1 wherein A is zinc.
3. The process of claim 1 wherein A is arsenic.
4. The process of claim 1 wherein D is niobium.
5. The process of claim 1 wherein D is boron.
6. The process of claim 1 wherein D is antimony.
7. The process of claim 1 wherein n-butane is reacted.
8. The process of claim 7 wherein the catalyst is $Zn_{0.2}V_{1.0}Nb_{1.2}O_x$.
9. The process of claim 7 wherein the catalyst is $Zn_{0.2}V_1B_{1.2}O_x$.

* * * * *

UNITED STATES PATENT OFFICE
CERTIFICATE OF CORRECTION

Patent No. 4,052,418                 Dated October 4, 1977

Inventor(s) D. D. Suresh et al.

It is certified that error appears in the above-identified patent and that said Letters Patent are hereby corrected as shown below:

Column 2:   Line 26, "Example" should be --Examples--

Column 2:   Line 64, "of" should be --to--

Column 3:   Line 63, "290°" should be --290°C.--

Signed and Sealed this

Twentieth Day of June 1978

[SEAL]

Attest:

RUTH C. MASON
*Attesting Officer*

DONALD W. BANNER
*Commissioner of Patents and Trademarks*